United States Patent [19]
Barry

[11] Patent Number: 5,857,998
[45] Date of Patent: Jan. 12, 1999

[54] STENT AND THERAPEUTIC DELIVERY SYSTEM

[75] Inventor: James Barry, Marlboro, Mass.

[73] Assignee: Boston Scientific Corporation, Natick, Mass.

[21] Appl. No.: 867,292

[22] Filed: Jun. 2, 1997

Related U.S. Application Data

[63] Continuation-in-part of Ser. No. 507,844, Jul. 27, 1995, Pat. No. 5,685,847, which is a continuation of Ser. No. 268,999, Jun. 30, 1994, Pat. No. 5,439,446.

[51] Int. Cl.$^6$ .................................................. A61M 29/00
[52] U.S. Cl. ........................................... 604/96; 606/194
[58] Field of Search .............................. 604/96, 101, 102, 604/52, 53, 103, 104, 49, 157–163, 8, 28; 606/192, 193, 194

[56] References Cited

U.S. PATENT DOCUMENTS

| | | | |
|---|---|---|---|
| 4,423,725 | 1/1984 | Baran et al. | 128/207.15 |
| 4,690,684 | 9/1987 | McGreevy et al. | 623/12 |
| 4,824,436 | 4/1989 | Wolinsky | 604/53 |
| 4,832,688 | 5/1989 | Sagae et al. | 604/53 |
| 4,922,905 | 5/1990 | Strecker | 606/195 |
| 4,950,227 | 8/1990 | Savin et al. | 604/8 |
| 5,026,377 | 6/1991 | Burton et al. | 606/108 |
| 5,059,211 | 10/1991 | Stack et al. | 606/198 |
| 5,108,416 | 4/1992 | Ryan et al. | 606/194 |
| 5,135,484 | 8/1992 | Wright | 604/28 |
| 5,158,548 | 10/1992 | Lau et al. | 604/96 |
| 5,234,457 | 8/1993 | Andersen | 606/198 |
| 5,242,399 | 9/1993 | Lau et al. | 604/104 |
| 5,254,098 | 10/1993 | Wang | 604/96 |
| 5,405,322 | 4/1995 | Lennox et al. | 604/53 |
| 5,439,446 | 8/1995 | Barry | 604/96 |

*Primary Examiner*—John D. Yasko
*Attorney, Agent, or Firm*—Pearson & Pearson

[57] ABSTRACT

Apparatus and a method for treating an irregularity in a wall of a vessel of a patient defined by an irregular or afflicted wall portion with adjacent normal wall portions comprises a catheter having a distal end portion for being guided through the vessel to the site of the irregularity. A balloon associated with said distal end portion of the catheter for selective inflating to contact the walls of the vessel urges a stent carried by the distal end portion of the catheter in a constricted condition for passage through the vessel into an expanded form with the stent spanning the afflicted wall portion and contacting the adjacent wall portions. The catheter is formed with lumens for inflating the balloon, for receiving a guidewire for guiding the catheter through the vessel, and for connecting a port in the catheter proximate the afflicted wall portion to enable delivery of a therapeutic agent into the vessel to contact the stent and the irregular wall portion.

26 Claims, 6 Drawing Sheets

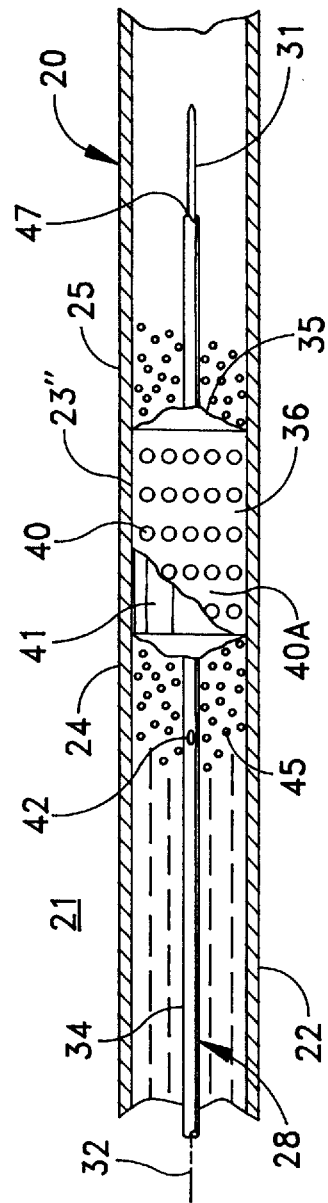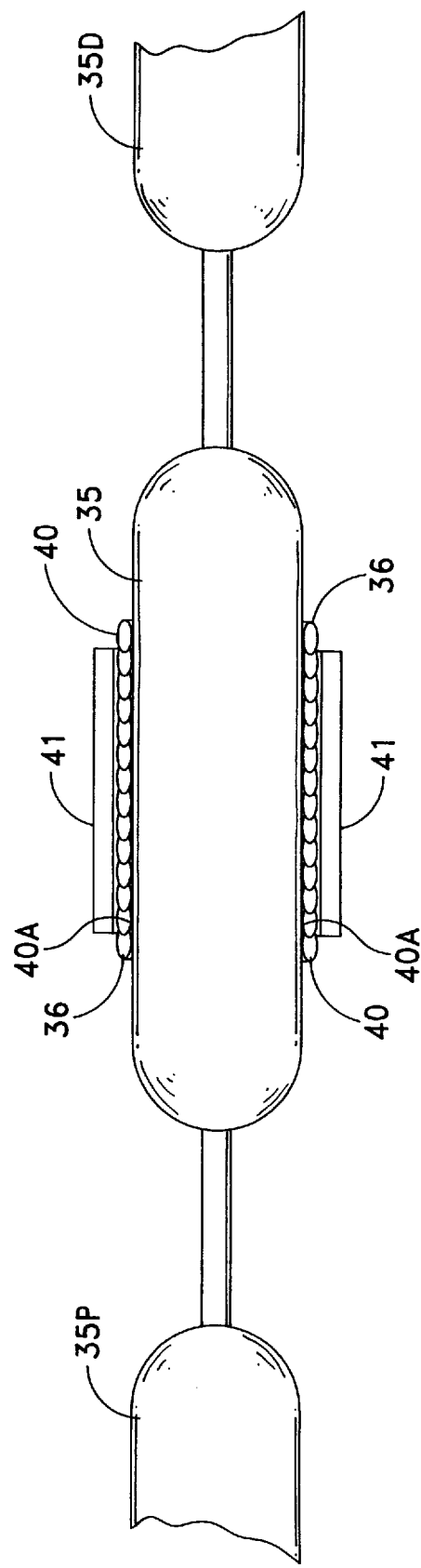

STENT AND THERAPEUTIC DELIVERY SYSTEM

CROSS REFERENCE TO RELATED APPLICATION

This is a continuation in part of application Ser. No. 08/507,844 filed Jul. 27, 1995 now U.S. Pat. No. 5,685,847, for a Stent and Therapeutic Delivery System which is a continuation of Ser. No. 08/268,999 filed Jun. 30, 1994 for a Stent and Therapeutic Delivery System (now U.S. Pat. No. 5,439,446 granted Aug. 8, 1995) which applications are all assigned to the same assignee as the present invention.

BACKGROUND OF THE INVENTION

1. Field of the Invention

The present invention generally relates to stents positionable within the body of a patient and more particularly relates to a stent for delivering a therapeutic agent therefrom and a method and system for delivery of a therapeutic agent to replenish the stent.

2. Description of Related Art

Physicians often use medical guidewires and catheters in combination. Medical guidewires are devices navigable through narrow passages in the body such as vessels, tubes, ducts, passages and the like, hereinafter collectively referred to as vessels. A physician controls the position and travel of a distal end of the guidewire by manipulating a steering mechanism at a proximal end outside the body. In other applications the physician guides the catheter through a laparoscope or endoscope. Medical catheters generally comprise hollow, flexible tubes that convey fluids, such as contrast, embolic, or pharmacological agents, to or from a vessel within a body.

Typically in transluminal procedures, a physician inserts and directs a medical guidewire through a vessel in a patient's body. The physician monitors the travel of the guidewire by a fluoroscope or other known device. Once positioned proximate the desired area, a steering mechanism is removed from the guidewire and a medical catheter is inserted into the vessel along the guidewire. Other procedures are also well known for directing catheters or similar devices into larger vessels of the body such as the esophagus.

Often these catheters include specialized attachments for providing different treatment modalities. For example, the following references disclose catheters with attachments for administering a therapeutic agent and performing balloon therapy:

| | | |
|---|---|---|
| 4,824,436 | (1989) | Wolinsky |
| 4,832,688 | (1989) | Sagae et al. |
| 5,254,089 | (1993) | Wang |
| 08/105,737 | (1993) | Lennox et al. |

U.S. Pat. No. 4,824,436 to Wolinsky discloses a multi-lumen catheter having opposed ring balloons positionable on opposite sides of a plaque formation in a blood vessel. Inflation of the ring balloons define an isolated volume in the vessel about the plaque. Heparin is then injected into the volume between the ring to assist the body in repairing the plaque deposit. This patent also discloses a central balloon which can be employed to rupture the plaque prior to inflation of the ring balloon.

U.S. Pat. No. 4,832,688 to Sagae et al. discloses a multi-lumen catheter having an occlusion balloon positionable distally of a tear in a vessel wall. Inflating the balloon occludes the vessel and isolates at the tear. A therapeutic agent, such as heparin or thrombin, injected from the catheter into the volume reduces the risk of thrombosis or restenosis. The balloon is then deflated and moved adjacent the rupture and reinflated to repair the ruptured wall by coagulation of blood thereat.

U.S. Pat. No. 5,254,089 discloses a balloon catheter having an array of conduits disposed within the outer wall of the balloon. The conduits include apertures in the other wall for delivery of medications through the wall of the balloon into the body of a patient. This type of balloon is often referred to as a channeled balloon.

U.S. application Ser. No. 08/105,737 to Lennox et al., discloses catheters having spaced balloons for treating aneurysms. The inflated balloons define an isolated volume about the aneurysm. A port connects a vacuum source to evacuate the volume and draw the aneurysmal wall toward its ordinary position. Inflating a third balloon with a heated fluid to contact the aneurysmal wall effects the repair.

Therapeutic agent and balloon delivery systems must meet certain criteria. That is, the cross-sectional dimension of the catheter must be minimized to enable transit through the vessel while also having sufficient dimension to enable fluid flow to selectively inflate and deflate the balloon, guidewires to pass therein, and therapeutic agents to flow therethrough for delivery along the catheter. Catheters must also have sufficient internal rigidity to prevent collapse of the lumens while having sufficient flexibility for passage along vessels.

The following references disclose stent delivery systems:

| | | |
|---|---|---|
| 4,690,684 | (1987) | McGreevy et al. |
| 4,922,905 | (1990) | Strecker |
| 4,950,227 | (1990) | Savin et al. |
| 5,059,211 | (1991) | Stack et al. |
| 5,108,416 | (1992) | Ryan et al. |
| 5,158,548 | (1992) | Lau et al. |
| 5,234,457 | (1993) | Anderson |
| 5,242,399 | (1993) | Lau et al. |

Stent delivery systems, as disclosed by the Lau et al. and Ryan et al. patents, often include a catheter supporting a compacted stent for transport in a vessel and an expansible device for expanding the stent radially to implant the stent in the vessel wall. After removal of the catheter, the expanded stent keeps the vessels from closing.

The McGreevy et al. patent discloses a stent formed of biologically compatible material, such a frozen blood plasma or the like. According to McGreevy et al., a stent of this type carried by a catheter may be inserted into opposed ends of a ruptured vessel to support the separated vessel walls while the ends are bonded together. Once deployed, the heat from the bonding operation and the body eventually melt the stent and clear the vessel.

The Strecker, patent describes a stent and delivery system. The stent is knitted from metal or plastic filaments and has a tubular structure. The delivery system includes a balloon catheter and a coaxial sheath. The catheter supports and carries the compacted stent to a site within the body. The sheath covers the stent preventing premature deployment and facilitating transit of the stent through passages in the body. Exposure of the stent by moving the sheath axially with respect to the catheter and expansion of a balloon urges the stent into contact with the walls of the vessel. Deflation of the balloon frees it from the stent and enables withdrawal from the vessel of the delivery system.

In the Savin et al. patent a stent delivery system includes a catheter having an expansible distal portion, a stent carried thereon in a contracted position for expansion thereby and sleeves that overlie the end portions of the stent. The sleeves protect the vessel and the stent during transit without substantially inhibiting deployment of the stent.

The Stack et al. patent discloses a stent delivery system comprising a catheter for delivering a compressed stent on a balloon or mechanical extension to the locus of a stenotic lesion. The balloon or mechanical extension proximate the distal end expands the stent and deflation of the balloon or retraction of the mechanical extension permits withdrawal of the distal end of the catheter through the stent. The stent comprises bioabsorbable porous material that reduces the likelihood of embolization and promotes tissue ingrowth in order to encapsulate the stent.

In accordance with the Anderson patent a stent delivery system includes a dissolvable material that impregnates a self-expanding stent in a compacted form. In one embodiment the removal of a sheath exposes the stent to body heat and liquids so that the material dissolves and the stent expands into a deployed position.

Stent delivery systems used in such procedures generally include catheters with selectively expansible devices to deliver and expand a contracted "stent" or restraints that can be removed to allow a self-expanding stent to assure an enlarged or expanded configuration. Stents are known and have a variety of forms and applications. For example, stents serve as prostheses and graft carriers in percutaneous angioplasty. Stents used as an endoprothesis and graft carriers to which the present invention relates usually comprise radially expansible tubular structures for implant into the tissue surrounding "vessels" to maintain their patency. As is known, such stents are utilized in body canals, blood vessels, ducts and other body passages, and the term "vessel" is meant to include all such passages.

Like the previously described therapeutic agent and balloon therapy systems, stent delivery systems must conform to several important criteria. First, it is important to minimize the transverse dimension of the delivery system, so the stent must be capable of compaction against a delivery device, such as a catheter. Second, the delivery system must facilitate the deployment of the stent once located in a vessel. Third, the stent delivery system must easily disengage from the stent after the stent is deployed. Fourth, the procedure for removing the delivery system from the body must be straightforward. Fifth, the delivery system must operate reliably.

It has been found that the administration of therapeutic agents with a stent can reduce the risks of thrombosis or stenosis associated with stents. Stents administered along with seed cells, such as endothelial cells derived from adipose tissue, can accelerate the reformation of an afflicted area. Likewise, tears or other vessel damage associated with balloon angioplasty can be reduced by a deployed stent used in combination with a therapeutic agent.

When both therapeutic agent and stent therapies are required, a physician generally (1) steers a guidewire to the treatment locus, (2) guides a catheter over the guidewire, (3) operates the catheter to provide the first stage of treatment, (4) inserts an exchange guidewire to the guidewire, (5) withdraws the catheter, (6) guides a second catheter over the guidewire, and (7) operates the second catheter to provide the second stage of treatment. After this, the physician withdraws the guidewire, if not previously removed, and the catheter from the body of the patient.

U.S. Pat. No. 5,439,446 to James Barry the inventor of the present invention and commonly assigned discloses a stent delivery system that incorporates a drug delivery system in the catheter. This device permits the surgeon to use one catheter to deliver both the stent and the therapeutic agent at a selected site in the patient's body.

Other references disclose the use of stents that release therapeutic agents associated with a deployed stent over time. For example U.S. Pat. No. 5,234,457 to Andersen commonly assigned as this invention discloses stents impregnated with a gelatin that enables the release of the stent. It is suggested that the gelatin could entrain a therapeutic agent that dispenses as the gelatin dissolves.

These references thus provide the ability to deliver stents and therapeutic agents to an afflicted site within a patient's body and even enables the dispersion of the therapeutic agent from the stent over time. However, if additional therapeutic agent is needed at the site another catheter must be inserted to deliver the therapeutic agent or by generally introducing the additional therapeutic agent to the vessel such as by injection in the case of a blood vessel or by bathing the esophagus for example.

In some cases where a slow release of the therapeutic agent is desired, as by the release of a therapeutic agent entrained in a gelatin or other hydrophilic or hydrophobic polymers on a stent. Once the therapeutic agent was delivered, replenishment required one of two procedures. In one, a new stent was inserted to be adjacent the old stent. Sometimes this reduced the effectiveness of the therapeutic agent, particularly when the area of treatment was displaced from the second stent. An alternative that overcame that problem was substituting a new stent for the old stent. It is true that percutaneous transluminal procedures and other procedures involving the insertion of stents into the body have improved in recent years. Likewise the reduction in the size of the instruments inserted into the patient reduces the risk of damage. However, it is still a fact that each insertion and extraction risks further damage to afflicted areas and damage to otherwise unaffected areas through which the instruments pass and can add to patient trauma. Moreover, insertion and withdrawal of additional instruments in sequence increases the time of the physician, staff, and medical facility, and the cost of multiple instruments. Thus, reducing the number of instruments and the overall size of the instruments necessarily inserted and withdrawn from a patient, the steps required by the processes, and the overall size of each of the instruments is generally preferred.

Thus, the above-described references generally disclose various forms stents and delivery systems for treatments or therapies using a catheter in percutaneous transluminal procedures and other internal procedures. Some combined with stent delivery systems, which may include a balloon for deploying the stent, while others combine balloon therapy and therapeutic agent delivery systems. Still others of the references disclose a stent delivery system combined with a therapeutic delivery system or a stent that actually enables the slow release of a therapeutic agent carried by the stent. However, none of these references disclose a stent that enable both the release of a therapeutic agent therefrom and the charging or recharging of the stent with a therapeutic agent once positioned within the body to permit delivery of therapeutic agent to replenish a stent. None provides a structure for improving the efficiency of percutaneous transluminal procedures and other internal procedures by providing a stent for dispensing a therapeutic agent that can receive additional therapeutic agents in vivo and a therapeutic agent delivery system for replenishing the therapeutic agent dispensed from the stent. None disclose a delivery system and method capable of replenishing a therapeutic agent after it has been depleted from an original supply.

SUMMARY

Therefore, it is an object of this invention to provide a method and apparatus for stent and therapeutic agent treatments by a stent with a replenishable reservoir of therapeutic agent It is another object of this invention to provide a method and apparatus for charging and recharging with a therapeutic agent a therapeutic agent delivery stent positioned within a patient whereby the stent can continue to dispense a therapeutic agent.

It is another object of this invention to provide a therapeutic agent delivery system adapted for replenishing a therapeutic agent reservoir of a deployed stent.

Yet another object of this invention is to provide a method and apparatus which enables delivery of a therapeutic agent to an afflicted portion of a vessel in a patient after depletion of an initial volume of therapeutic agent carried by the stent.

It is a further object of this invention to provide a method and apparatus for delivering a stent and therapeutic agent to a vessel which is relatively simple and inexpensive to produce and use.

In accordance with one aspect of this invention a stent assembly for deployment within a patient's body includes a frame that defines a stent assembly form. The frame supports a therapeutic agent reservoir characterized by allowing therapeutic agent to seep from the reservoir. A port connected to the reservoir allows the introduction of the therapeutic agent into the reservoir subsequent to the deployment of the stent assembly in the patient's body.

In accordance with another aspect of this invention a stent assembly for deployment within a patient's body includes a frame that defines the shape of the stent assembly. A reservoir carried by the frame delivers the therapeutic agent from the stent assembly. A delivery system connects to the reservoir means to enable the addition of the therapeutic agent to the reservoir means in vitro.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 2A is an enlarged view, partially in cross section, of a portion of a balloon and stent assembly constructed in accordance with this invention;

FIG. 5 depicts a repair vessel and the delivery system of FIG. 2 at final stage of the treatment modality prior to its removal from the vessel;

DESCRIPTION OF ILLUSTRATIVE EMBODIMENTS

Figure 1:
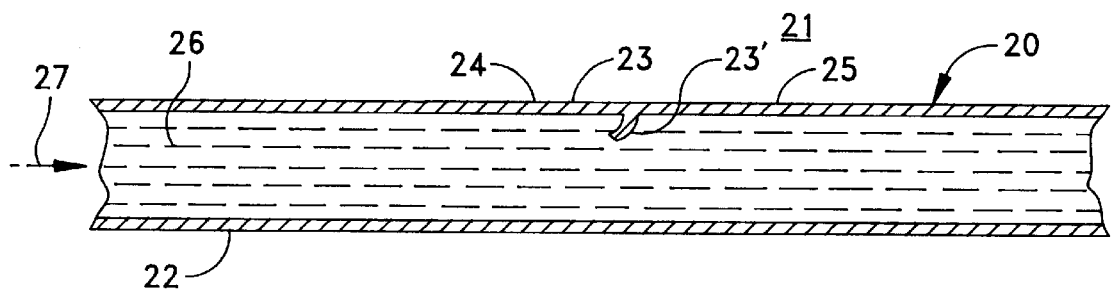
FIG. 1 depicts a single passage vessel with an irregularity comprising a tear in the wall of the vessel.

FIG. 1 depicts, in simplified form, a single-passage, tubular vessel 20 through tissue 21, such as peri-arterial tissue, defined by a vessel wall 22. Although FIG. 1, and the other similar figures, depict a vessel wall as comprising a single homogeneous layer, it will be recognized that an actual vessel wall has multiple layers. However, this invention can be understood by referring to the simplified, homogenous representation in the figures. Furthermore it should be appreciated that the vessel 20 is intended to be representative generally of any of the diverse passageways found in a patient's body.

FIG. 1 illustrates an irregularity or abnormality in the wall of the vessel 20 at an afflicted or irregular wall portion 23 in the vessel wall 22 that is disposed between essentially normal wall portions 24 and 25. In this case, the irregular wall portion 23 includes a flap 23' that can develop due to the weakening and/or stretching of the walls in otherwise normal wall 22. Such flaps frequently result either naturally or from, for example, stretching by dilation of the vessel during balloon angioplasty. In the esophagus such tears can result from the passage of other objects during ingestion or from tumor growth. Tears of this kind can also appear in the intestinal tract.

For ease of understanding the invention, the vessel 20 will be described in terms of a blood vessel. Blood 26 flows in a direction represented by arrow 27 within the vessel 20. If left untreated, the flap 23' can grow in size and occlude the vessel due to coagulation of blood thereat. Such flaps may also result in ruptures of the vessel. Other abnormalities in vessels of the type to which the present invention is applicable include aneurysms, ruptures, stenosis, and the like. Additionally the stent according to this invention can be used as a site delivery vehicle that over time dispenses a therapeutic agent proximate a desired location such as a tumor, other abnormality or other site selected for the delivery of such agent.

Figure 2:
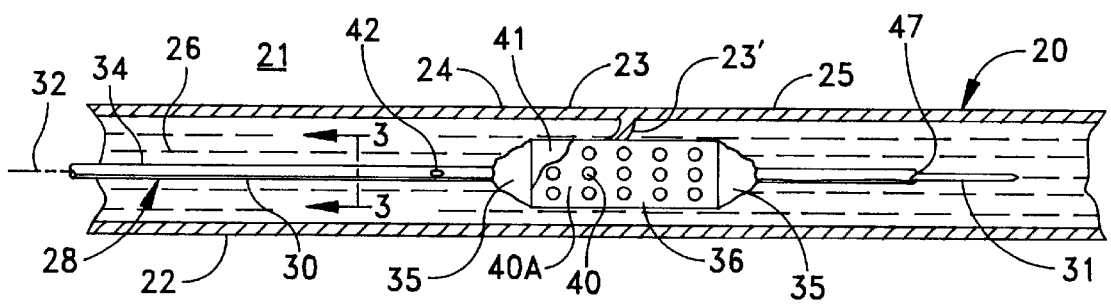
FIG. 2 depicts in side elevation an embodiment of a delivery system constructed in accordance with this invention for treating the irregularity in the vessel of FIG. 1 at a first stage in a treatment modality.
Figure 3:
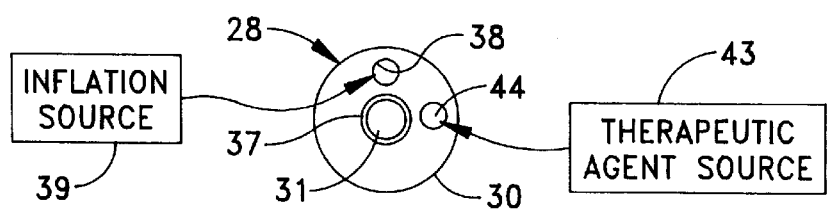
FIG. 3 is a view, partly in schematic and partly in perspective form, of portions of the delivery system taken along lines 3—3 in FIG. 2.

FIGS. 2 and 3 depict a delivery system 28 in accordance with this invention that includes a medical catheter 30 extending over a predisposed guidewire 31 generally along an axis 32. The catheter 30 includes a proximal end portion (not shown) and a distal end portion 34. The distal end portion supports an expansible balloon 35 with an expandable stent 36 carried in a constricted or compacted condition on the balloon. It will be understood that various other means for expanding or enabling the expansion of the stent 36 may be employed without departing from the scope of this invention. A plurality of lumens in the catheter 30 include a guidewire lumen 37 through which the guidewire 31 extends and an inflation lumen 38 connecting the balloon 35 with a inflation source 39 for selectively inflation and deflation.

The stent 36 as depicted in FIGS. 2, 2A, 4 and 5 includes pores 40 through a frame or structure 40A that defines the overall shape of the stent 36 and underlies and supports a membrane 41. The pores or apertures 40 as depicted in FIG. 2A may be provided to promote tissue ingrowth as well as to enable flow to or from branches of the vessel connecting thereat. Those skilled in the art will recognize, however, such apertures may in various procedures be unnecessary or, even, counterproductive. The stent 36 may be formed in other known stent constructions (e.g., interlocking loops or mesh formed by filaments, etc.) and materials such as various plastic or metals, including tantalum, stainless steel or nitinol wire that define the frame 40A, provided that the structure defining the stent can support the overlying membrane.

In accordance with this invention a membrane 41 overlies at least a portion of the frame 40A or preferably as shown in FIGS. 2 and 3 the entire frame. The membrane 41 is permeable to the therapeutic agent and defines a reservoir or means for enabling the passage or seepage of the therapeutic agent into the vessel 20 over time. The membrane 41 preferably comprises a hydrophilic or hydrophobic polymer with a pore size that enables the therapeutic agent 42 to seep through the membrane 41. It will also be recognized that the membrane could be formed of other materials.

Figure 4:
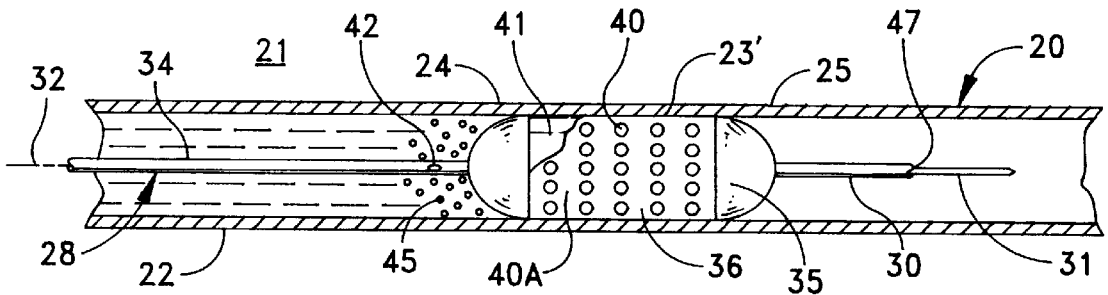
FIG. 4 depicts the delivery system of FIG. 2 at an intermediate stage of the treatment modality.

FIG. 4 depicts the apparatus 28 after the inflation source 39 expands the balloon 35 toward the wall 22 of the vessel 20. Expansion of the balloon 35 urges the stent 36 into an expanded, deployed condition so that it spans the irregular wall portion 23 and contacts both the adjacent normal wall portions 24 and 25. Inflation of the balloon 35 in this case occludes the vessel 20 and defines a portion or volume 51 of the vessel that is proximal the balloon 35, the stent 36 and the irregular wall portion 23 and that is relatively isolated from the portion of the vessel distally of the balloon 35. Thus, in this embodiment the balloon is part of both balloon means associated with the catheter for selective inflating to contact the walls of the vessel and means associated with the catheter for enabling the deployment of the stent in its expanded form.

Referring again to FIGS. 2 and 3, the catheter 30 has a port 52 positioned proximally of the balloon 35. A therapeutic agent source 53 and the port are connected by lumen 54 to inject a therapeutic agent 42 into the volume 51. In this case, the port 52 and lumen 44 comprise means associated with the catheter for delivering a therapeutic agent proximal the inflated balloon and proximate the afflicted wall portions so that the agent contacts the stent in its expanded form. If the membrane 41 has not previously been charged with therapeutic agent, the membrane tends to absorb the agent. To improve the infiltration of the therapeutic agent into the membrane, balloons may be provided proximally and distally of the balloon 35. These added balloons, like balloons 35P and 35D in FIG. 2A, preserve the isolated volume 51 when the balloon 35 deflates. These added balloons, when inflated, can also reduce the size of the volume creating an over pressure to further aid in the infiltration of the therapeutic agent into the membrane 41.

The therapeutic agent 42 preferably includes an active agent, such as a drug or endothelial cells. Examples of the drugs which would be appropriate active agents include antithrombins such as heparin and derivatives thereof; antiplatelet agents such as PPACK, iloprost, integrelin, and chimeric antibodies such as c7E3; genetic therapies including antisense oligonucleotides and various gene constructs; antipoliferatives such as angiopeptin; chemotherapeutic agents such as paolitaxel; antioxidants such as probucol; vasorelaxants such as nitroglycerin and papaverine or ones with multiple effects such as nitric oxide; and the like. The active agent would preferably have an affinity for the afflicted tissue, the stent 35, or both, or the active agent could be encapsulated or attached to albumin, cells, fibrin and other matrix proteins, platelets, various natural and synthetic polymers, liposomes, red blood cells or the like having such an affinity if desired. In such case, the active agent, whether directly or due to its encapsulation, would attach on or near the irregular wall portion 23.

If the membrane 41 is formed of a hydrophilic material, and certain therapeutic agents are introduced into the isolated volume 51, the hydrophilic material initially absorbs a portion of the therapeutic agent. When the bounds on the isolated volume are thereafter removed and the therapeutic agent in the blood disperses, the hydrophilic membrane will release the absorbed therapeutic agent over time. With such a device it will be further evident that replenishment can be accomplished by relocating a balloon such as shown in FIG. 1 in the vessel such that the central balloon 35 is located under the stent. The proximal and distal balloons then would be inflated to form the isolated volume and additional therapeutic agent could be delivered, with the cycle repeating thereby a portion of the therapeutic agent would be absorbed in the membrane 41. As an alternative, it would also be possible to recharge the structure through a dual balloon catheter in which two balloons, such as balloons 35D and 35P in FIG. 2A, form the isolated volume inclusive of the membrane. Alternatively a single balloon structure formed of a channel or other drug delivery type balloon could be expanded at the membrane to direct therapeutic agent to the membrane 41 for absorption therein.

Moreover, encapsulating the active agent in a dissolving material, such as albumin or various polymers which would effect a continuing release of the active agent proximate the irregular wall portion 23 during the patency of the encapsulating agent. Examples of such polymers would include pluronics gels, citric acid cycle polymers, such as polylactic acid, polyglycolic acid and derivatives thereof, polyanhydrides, polyphosphazenes, polysaccarides, such as alginic acid, chitin and derivatives thereof, collagen and derivatives thereof, and glycosaminoglycans such as hyaluronic acid and derivatives thereof. In other modalities in which endoscopic procedures are involved, such a catheter as incorporates this invention can be inserted through a working channel in the ordinary manner and directed to a desired location.

Use of the present invention to treat irregularities in vessel walls generally comprises several stages of treatment. The steps usually include percutaneously inserting the guidewire 31 into a patient's vessel, guiding the guidewire to a position proximate the irregularity in the vessel 20, and inserting the guidewire lumen 37 of the catheter 30 over the guidewire 31 to enable the catheter to be directed to the irregularity, as represent in FIG. 2. Once the catheter 30 is positioned proximate the irregularity, the guidewire may be removed or otherwise remain.

Notwithstanding the modality used to locate the catheter, once located within a patient, the inflation of the balloon 35 to contact the wall 22 substantially occludes the vessel 20 and inhibits blood flow therethrough, as depicted in FIG. 4. Inflation of the balloon 35 also urges the stent 36 from its compacted condition to its expanded, operative condition spanning the afflicted wall portion 23 and contacting the adjacent normal wall portions 24 and 25. In such a system a number of therapeutic agent delivery procedures could be utilized. The balloon 35 with its external membrane could be precharged to deliver a first therapeutic agent while a second therapeutic agent might be delivered from the source 43 in FIG. 3 thereby to perform two different drug therapies simultaneously. Alternatively the membrane could be formed to delay the release of the agent to perform two different procedures in sequence. Thereafter the first therapeutic agent or even another therapeutic agent capable of being absorbed in the membrane could be applied from the therapeutic agent source 43. In each of these cases, the deployed stent 36 holds the flap 23' (see FIG. 2) proximate the wall of the vessel 20. With the vessel occluded, as depicted in FIG. 4, therapeutic agent 42 from the source 43 (FIG. 3) enters the volume 51 proximally of the balloon 35 and the stent 36 at the port 52.

Deflation of the balloon 35, as depicted in FIG. 5, enables the therapeutic agent 42 to contact the stent 36 and afflicted wall portion 23 through the pores 40 and enables retraction of an extreme distal end 47 of the catheter through the stent and ultimately from the patient. After the deployment of the stent 36 and deflation of the balloon 35, the catheter 34 may be moved within the vessel to other sites for either or both therapeutic agent and balloon therapy. That is, thereafter the balloon 35 serves as a standard inflatable, catheter-mounted balloon with the port 52 also providing delivery of therapeutic agents as desired.

Figure 6:
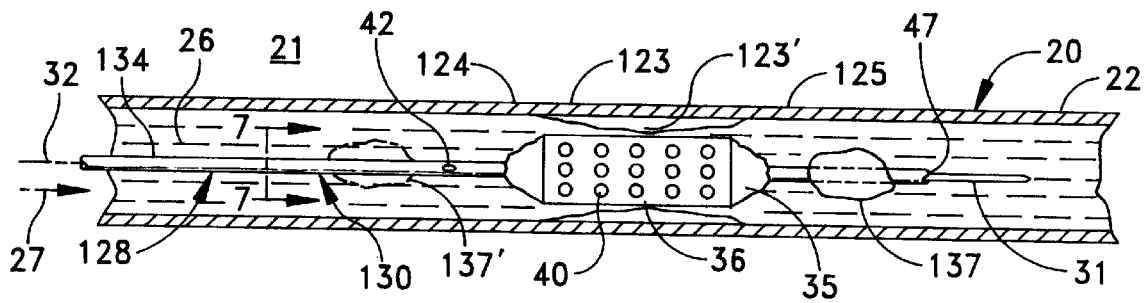
FIG. 6 depicts in side elevation another embodiment of a delivery system similar to FIG. 2 for treating an irregularity the vessel of FIG. 1.
Figure 7:
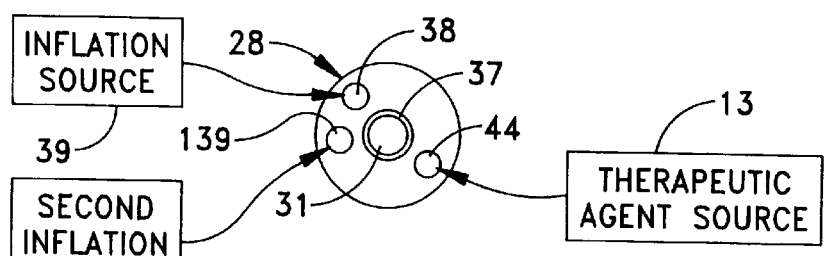
FIG. 7 is a view, partly in schematic and partly in perspective form, of portions of the delivery system of FIG. 6 taken along lines 7—7 in FIG. 6.

FIGS. 6 and 7 depict another embodiment of this invention as applied to the vessel 20 with an irregular wall portion 123 comprising an abnormal narrowing of the vessel or stenosis 123'. A delivery system 128 includes a catheter 130 having a distal portion 134. The catheter 130 carries the balloon 35 with the stent 36 for deployment within the vessel. The portion 134 also carries an inflatable balloon 137, which in this instance is positioned distally of the balloon 35, for occluding or substantially occluding the vessel. In some cases a second balloon 137' depicted in phantom lines may be positioned opposite the balloon 35 with respect to the first balloon 137 or even be used in place of the balloon 137.

Figure 8:
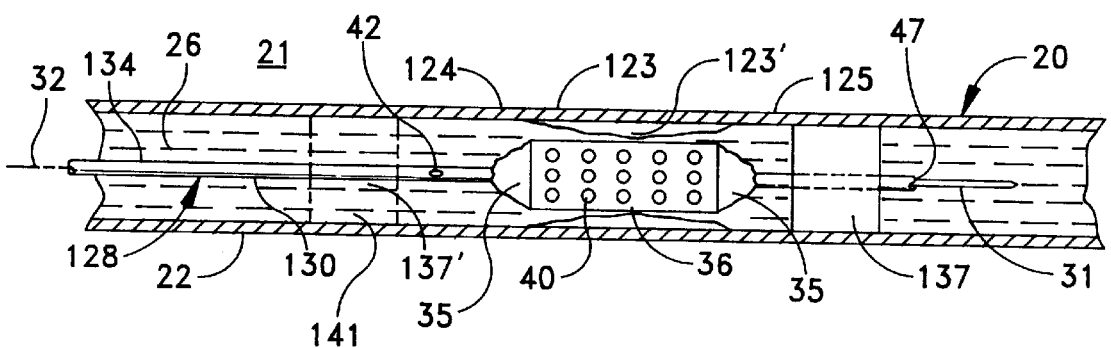
FIG. 8 depicts in side elevation the embodiment of FIG. 6 at a first stage in a treatment modality.

Referring to FIGS. 6, 7 and 8, a second inflation source 138 inflates the balloon 137 into contact with the vessel wall 22 by urging inflating fluid along a lumen 139. The inflated balloon 137 defines a volume 151 in the vessel 20 proximally of the balloon 127 which includes the wall portion 123. Use of the balloon 137' would isolate the volume 151 about the wall portion 123 in which the stent 36 would be positioned. The therapeutic agent 42 enters the volume 151 through the port 52 proximally adjacent the balloon 35. As previously discussed with respect to FIGS. 4 and 5, the therapeutic agent 42 preferably has an affinity for either or both the afflicted tissue and the stent 36.

Figure 9:
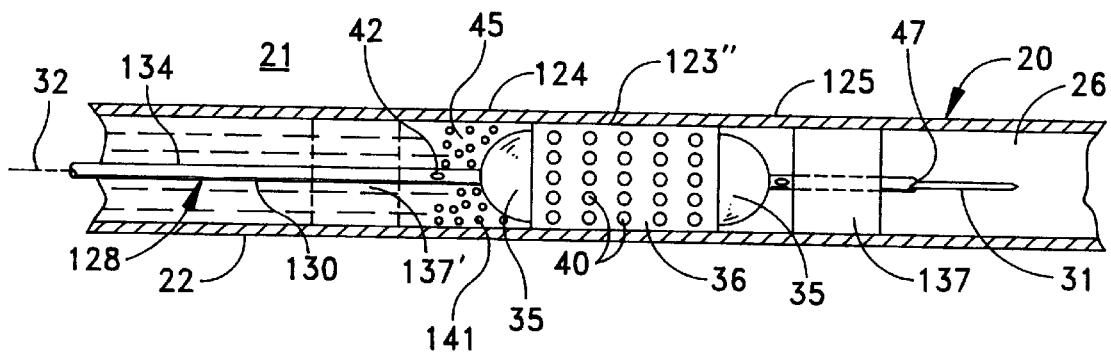
FIG. 9 depicts in side elevation the embodiment of FIG. 6 at an intermediate stage in the treatment modality.
Figure 10:
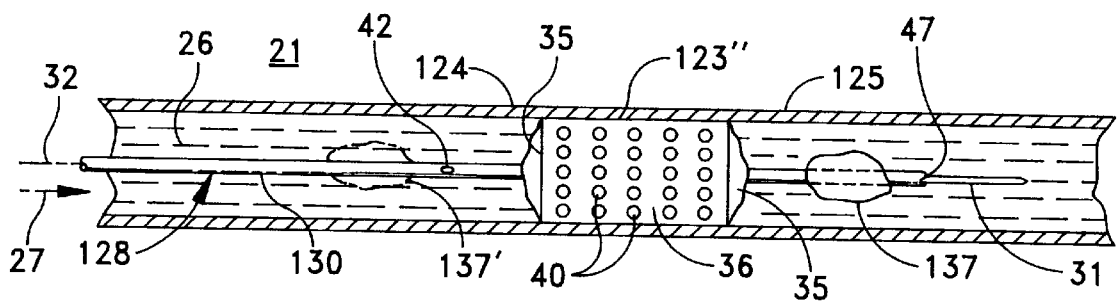
FIG. 10 depicts in side elevation the embodiment of FIG. 6 at a final stage of the treatment modality.

Referring to FIGS. 8 and 9 inflation of the balloon 135 urges the stent 36 from its compacted condition. The deployed, expanded stent 36 spans the afflicted wall portion 123 and contacts the adjacent normal wall portions 24 and 25 to urge the stenotic portion 123' into a substantially normal position indicated as wall portion 123". Introduction of the therapeutic agent 42 can occur prior to stent deployment, during stent deployment or after stent deployment, and the balloon 35 may be reinflated to aid disposition of the agent along the stent 36 and wall 123. Deflation of the balloons 137 and 35, as depicted in FIG. 10, enables retraction of the catheter 130 from the patient while the stent 36 remains at the repaired wall portion 123".

This embodiment has been described in terms of a four-lumen catheter, although it will be appreciated that various modifications can be made. For example, the balloons 35 and 137 can be inflated from a common source through a common lumen when independent inflation is not needed. Those skilled in the art will recognize that this embodiment can also be employed as a common angioplastic catheter for treating, for example, stenotic irregularities by dilation of the vessel proximate the stenosis.

Specifically, the balloon 137 enables the dilation of vessels to dilate a stenotic vessel in a known manner, as well as other therapies involving either or both balloon and therapeutic agent therapies. However, in situations in which an irregularity of the type adapted for treatment by stent therapy, such as a flap, rupture or other irregularity results from the balloon therapy or is detected during such therapy, in which such irregularity is detected during the balloon therapy, the present invention enables stent and therapeutic agent therapy without exchanging catheters or other delay. In such case, the catheter would be repositioned so as to enable the stent to be deployed at the irregular wall portion and the steps previously described would occur. Thus, this embodiment with a separate inflation balloon 137 permits a physician to provide balloon therapies, while also providing stent and therapeutic agent therapy as needed.

Figure 11:
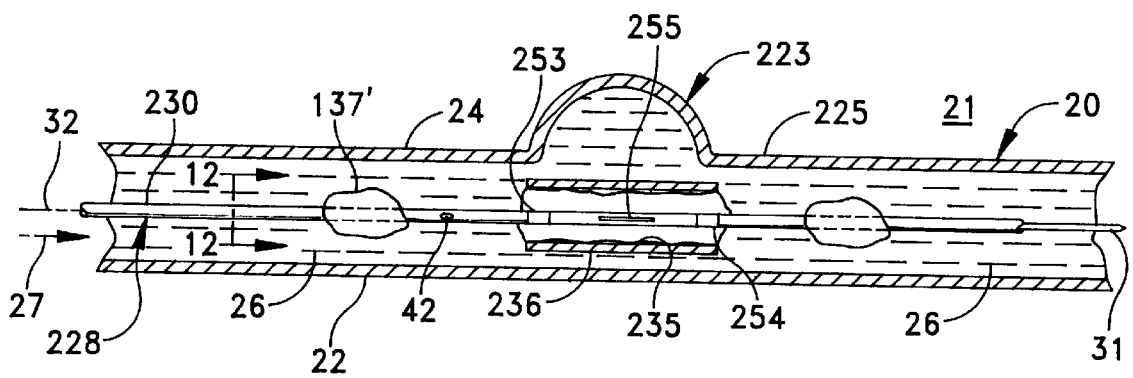
FIG. 11 depicts another embodiment of the delivery system of the present invention, similar to those of FIGS. 2 and 6, in the at a first stage in a treatment modality for treating an irregularity in the vessel of FIG. 1.
Figure 12:
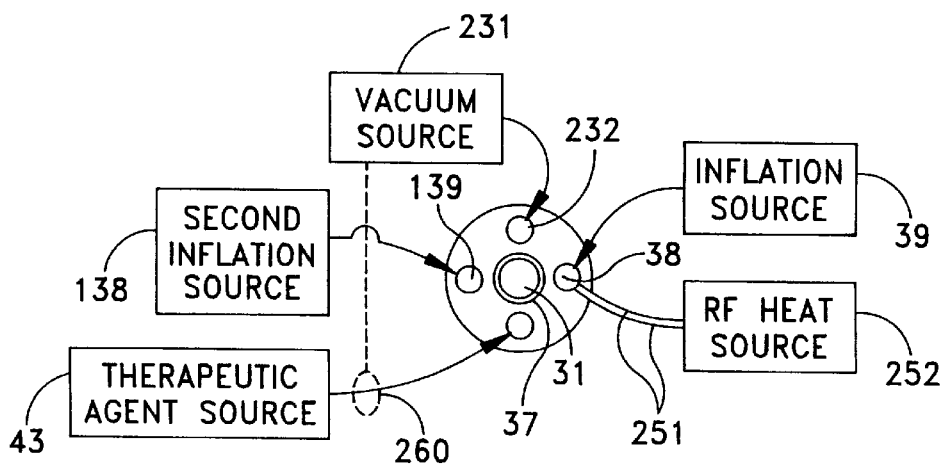
FIG. 12 is a view, partly in schematic and partly in perspective form, of portions of the delivery system of FIG. 11 taken along lines 12—12 in FIG. 11.

In FIGS. 11 and 12 the vessel 20 includes an aneurysmal wall portion 223 with a delivery system 228 for providing therapy for aneurysms positioned proximate thereto. The system 228 includes a catheter 230 having a deployment balloon 235 on which a stent 36 is carried for deployment.

Figure 13:
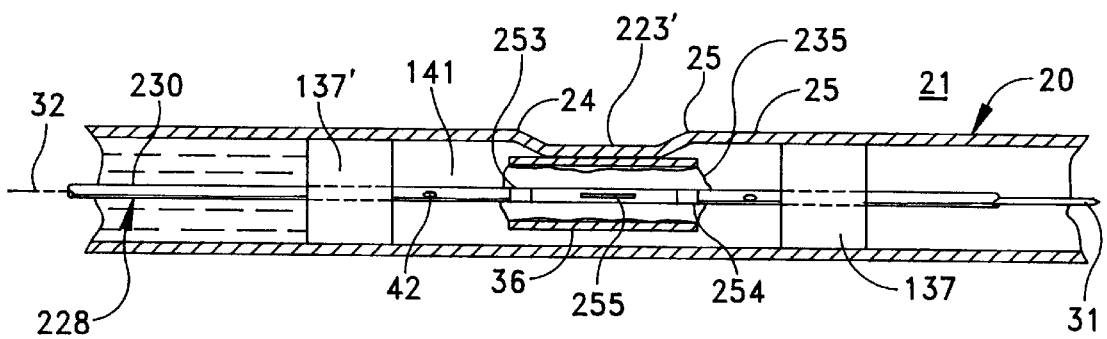
FIG. 13 depicts in side elevation the embodiment of FIG. 11 at a first stage in a treatment modality.

As depicted in FIGS. 12 and 13, a vacuum source 231 connected through lumen 232 to port 233 evacuates the isolated volume 151 defined between inflated balloons 137 and 137'. Evacuation of the volume tends to draw the blood 26 from the volume 151 and the aneurysmal wall portion 223 toward the catheter 230 proximate the original position of the portion in line with the wall portions 24 and 25, as represented by the portion 223'. The therapeutic agent source injects the therapeutic agent 42 into the volume 151 usually after evacuation, although it may also follow stent deployment.

Figure 14:
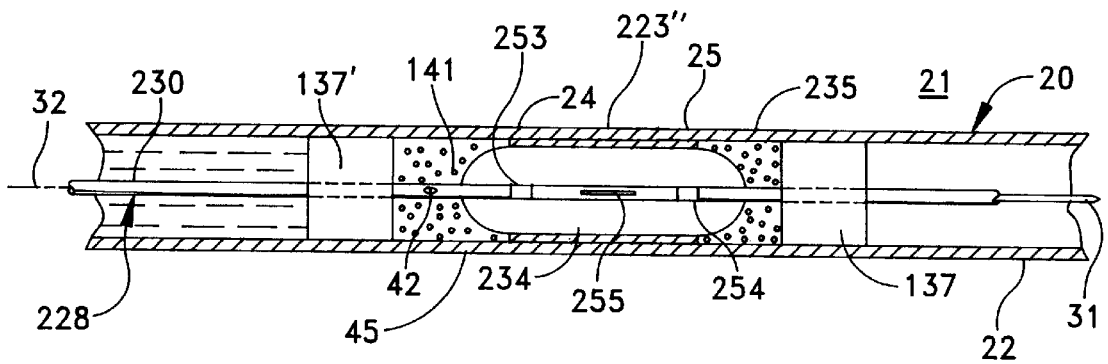
FIG. 14 depicts in side elevation the embodiment of FIG. 11 at an intermediate stage in the treatment modality.

Referring to FIGS. 12 and 14, ionizable fluid 234 directed from the inflation source 39 along lumen 38 inflates the balloon 235 to contact the vessel wall 22 and deploy the stent 35 which may be a standard stent or graft carrying stent. Conductors 251 carried in the lumen 38 connect an rf heating source 252 with spaced electrodes 253 and 254 on the catheter 230 internally of the balloon. The heating source 252 energizes the electrodes 253 and 254 with the resulting current between the electrodes 253 and 254 heating the liquid 234 within the balloon 235, the stent 35 and the surrounding tissue including the weakened aneurysmal wall 223.

This heat thermally coagulates the weakened aneurysmal wall 223. Specifically, thermal coagulation has the chronic effect of forming fibrous scar tissue in the weakened aneurysmal wall 223. This shrinks and thickens the aneurysmal wall 223 to reduce its compliance and arrest progression of the aneurysm formation which is further strengthened by the deployed stent 35. Preferable, a temperature sensor 255 connected through the conductors 251 to the rf heating source 252 provides a feedback control signal to accurately regulate the temperature of the liquid 48.

Figure 15:
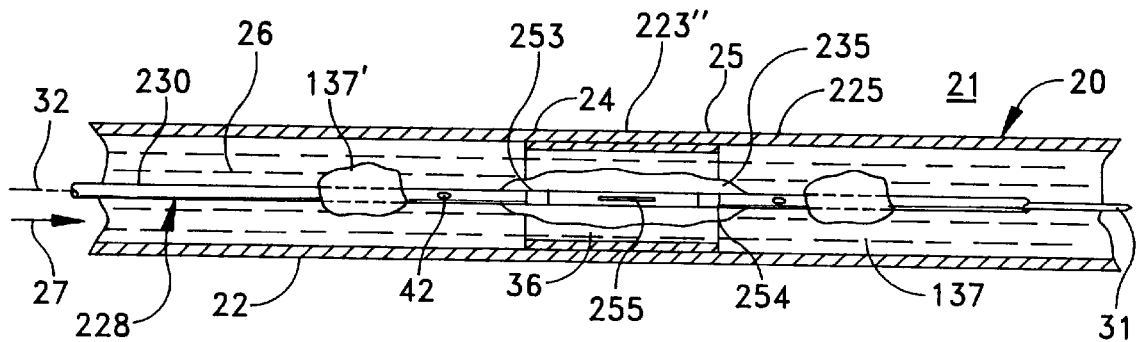
FIG. 15 depicts in side elevation the embodiment of FIG. 11 at a final stage of the treatment modality.

Upon completion of the treatment with the rf heating source 252 deenergized, the vacuum source 45 turned off, and the balloons 137 and 235 deflated, the delivery system 228 assumes the compact configuration depicted in FIG. 15. The blood 26 resumes flow in the direction 127 and the therapeutic agent 42 not adhering to the stent or wall 123' flows with the blood. Next a surgeon removes the apparatus 230 leaving the vessel 20 with a thickened and strengthened wall portion 223' with a stent 36 in place of the aneurysmal wall 223 of FIG. 13.

Stating that those skilled in the art will now appreciate that both with and without the rf heating the embodiment of FIGS. 11 through 15 enable a therapeutic agent to be administered and then be withdrawn using the vacuum source 45. For example, this can be particularly useful in cases where the therapeutic agent has particular toxic or other adverse effect on certain tissues of the body. Thus the physician can apply the drug to the affected area and then remove it to minimize any adverse impact from the therapeutic agent. In a case of an aortic aneurysm after evacuation, the physician can infuse a matrix protein or collagen to coat the graft for cell adherence in the wall of the graft. The vacuum is then used to suck out the free material. Thereafter, endothelial cells, which may be genetically altered are infused. These cells then bond to the protein matrix which preferably promotes cell growth and division of the infused endothelial cells.

The specific apparatus 228 in FIGS. 11 through 15 includes a catheter 230 with five discrete lumens. Certain functions of these lumens may be combined in a single lumen. For example, the vacuum source 231 and therapeutic agent source might connect directly to one lumen 44 by means of a valve 260. In addition, each of the individual components including the balloons 137 and the balloon 235 have conventional constructions. Apparatus for heating the liquid 234 in the balloon 235 through the use of rf energy applied to electrodes 253 and 254 and related systems including the temperature sensor 255 are also known in the art.

Figure 16:
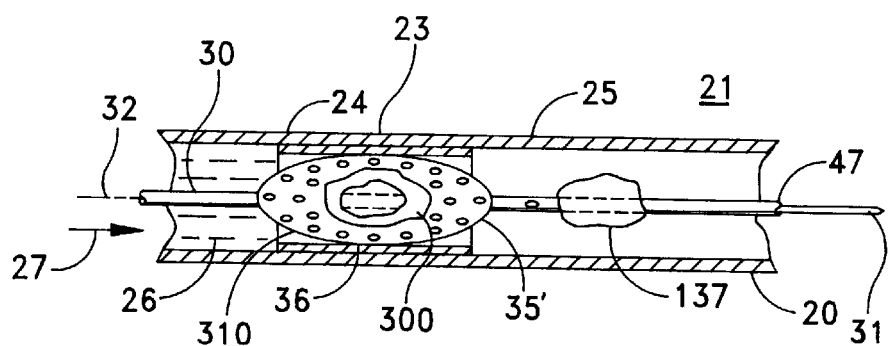
FIG. 16 depicts in side elevation an alternative balloon mounted on a catheter for use in the embodiments of the present invention.

As depicted in FIG. 16, a balloon for deploying the stent need not fully occlude a vessel 20 and may be combined with the means for delivering the therapeutic agent. Here, a balloon 35' mounted on the catheter 30 in the vessel 20 comprises an inner impermeable layer or surface 300 and an apertured or otherwise porous layer or outer surface 310 (e.g., a channeled balloon). Lumens (not shown), such as lumen 38 and 44 of FIG. 3, have ports between the catheter 30 and the inner surface 300 and the surface 310, respectively. Through these lumens, the inflation fluid expands the surface 300 and the therapeutic agent 42 is delivered interiorly of the outer surface 310. As previously discussed, the stent 36 may be mounted on an expansible balloon, which in this instance is the balloon 35', for deployment.

Continuing to refer to FIG. 16, the inflation lumen delivers the inflation fluid interiorly of surface 300 to inflate the balloon toward the walls of a vessel in which the balloon is disposed and to expand a stent mounted thereon. The delivery lumen delivers the therapeutic agent 42 intermediate the surfaces 300 and 310. Thus, the therapeutic agent 42 exits the balloon 35' through the apertures of the surface 310 to contact the stent 36 proximate thereto. It will be recognized that the apertured surface 310 comprises a port for the delivery of the therapeutic agent 42 proximate the stent. Additionally, the apertures in the surface 310 may be concentrated or entirely positioned in one area of the balloon 35'. Particularly, the apertures may be provided at the end of the balloon 35' closest the proximal end of the catheter.

Those skilled in the art will appreciate that, as discussed with respect to the embodiment of FIGS. 6 through 10, a second independent inflation balloon may be formed on the catheter 30 of FIG. 16 to provide a second means for dilating the vessel thereby. Additionally, the heating means of the embodiment of FIGS. 11 through 15 may also be included in either of such balloons, as appropriate for the application.

The means for expanding and deploying the stent the invention can include the stent itself. For example, certain stents react to heat or other conditions by expanding and deploying. Other stents expand and deploy upon release of a stent from removable sleeves. The apparatus shown in connection with the various figures is adapted for deploying such self-expanding stents. A removable sheath is disposed over the stent to protect the vessel and permit selective deployment of the stent. Employing such self-expanding stents eliminates the requirement for balloon expansion. However, the balloon still functions to occlude the vessel. Alternatively, as shown in FIGS. 11 through 15, the deployment balloon 35 of FIGS. 2 and 6, for example, can be provided with electrodes to heat a heat expansible stent to deploy the stent.

In summary, a delivery system according to each of the embodiments of this invention comprises a catheter having means for deploying an expandable stent and delivering a therapeutic agent for contacting the stent. Moreover, the operating techniques are analogous to standard medical procedures with respect to positioning the catheters in blood vessels, inflating the balloons, deploying the stents, and injecting therapeutic agents so the use of this apparatus is readily mastered. However, the apparatus eliminates the need for repetitive insertion of apparatus for different treatment modalities and reduces the risk of additional trauma to the patient. The invention also improves the treatment of patients by allowing combined modalities of treatment relatively concurrently, as well as successively. The invention also increases the efficiency of doctors, staff, and medical facilities. Moreover, by using bioabsorbable stents no foreign objects, such as clips or tubes, permanently remain permanently in the patient after treatment. The invention also provides delivery systems sized for the treatment of irregularities in both large and relatively small vessels.

What is claimed as new and desired to be secured by Letters Patent of the United States is:

1. A stent assembly for deployment within a patient's body comprising:

A. frame means for defining the form of the assembly;

B. means supported by said frame means for defining a therapeutic agent reservoir and for enabling the seepage of a therapeutic agent in the therapeutic agent reservoir therefrom; and C. port means connecting with said reservoir means for introducing a therapeutic agent into said therapeutic agent reservoir subsequent to deployment of the stent assembly in a patient's body.

2. An assembly as recited in claim 1 wherein said means for defining a therapeutic agent reservoir comprises a porous membrane whereby the therapeutic agent received in said membrane seeps through said membrane and into the patient's body.

3. An assembly as recited in claim 2 wherein said frame means comprises an expansible member adapted for insertion in a compact form into the patient's body and for deployment in an expanded form in the patient's body.

4. An assembly as recited in claim 3 wherein said porous membrane overlies said frame means whereby the therapeutic agent reservoir is contiguous with said frame means.

5. An assembly as recited in claim 4 wherein said porous membrane comprises a polymeric material.

6. An assembly as recited in claim 5 wherein said polymeric material is a hydrophilic polymer.

7. An assembly as recited in claim 5 wherein said polymeric material is a hydrophobic polymer.

8. An assembly as recited in claim 1 wherein said frame means comprises an expansible member adapted for insertion in a compact form into the patient's body and for deployment in an expanded form in the patient's body.

9. An assembly as recited in claim 8 wherein said means for defining the therapeutic agent reservoir overlies said frame means whereby the therapeutic agent reservoir is contiguous with said frame means.

10. An assembly as recited in claim 8 wherein said means for defining the therapeutic agent reservoir is formed of a hydrophilic material.

11. An assembly as recited in claim 1 wherein said means for defining the therapeutic agent reservoir is formed of a hydrophilic material.

12. A stent assembly for deployment within a patient's body comprising:

A. frame means for defining the shape of the assembly;

B. reservoir means carried by said frame means for delivering a therapeutic agent from said stent; and C. delivery means connected to said reservoir means for enabling addition of the therapeutic agent to said reservoir means in vivo.

13. A stent assembly as recited in claim 12 wherein said frame means comprises an expansible form for insertion into a patient's body in a compact condition and for deployment in an expanded condition.

14. A stent assembly as recited in claim 13 wherein said reservoir means overlies said frame means.

15. A stent assembly as recited in claim 14 wherein said reservoir means comprises a hydrophilic membrane overlying said frame means to define thereby a reservoir for receiving the therapeutic agent.

16. A stent assembly as recited in claim 15 wherein said delivery means is a port formed in said membrane.

17. A stent assembly as recited in claim 12 wherein said reservoir means overlies said frame means.

18. A stent assembly as recited in claim 15 wherein said reservoir means comprises a polymeric membrane overlying said frame means to define thereby a reservoir for receiving the therapeutic agent.

19. A stent assembly as recited in claim 18 wherein said polymeric membrane is composed of a hydrophilic material.

20. A stent assembly as recited in claim 18 wherein said polymeric membrane is composed of a hydrophobic material.

21. A stent assembly as recited in claim 16 wherein said delivery means is a port formed in said membrane.

22. A stent assembly as recited in claim 12 wherein said reservoir means includes a hydrophilic membrane supported by said frame means to define thereby a reservoir for receiving the therapeutic agent.

23. A stent assembly as recited in claim 22 wherein said delivery means is a port formed in said membrane.

24. A therapeutic agent delivery system for replenishing a reservoir of a replenishable stent comprising:

A. insertion means having a distal end for inserting within the body of a patient and a proximal end for control by an operator of said insertion means;

B. transfer means proximate the distal end of said insertion means for connecting with the reservoir;

C. lumen means in said insertion means for connecting said transfer means with the proximal end of said insertion means; and D. means associated with the proximal end of said insertion means for urging a therapeutic agent through said lumen means and transfer means to enable thereby replenishment of the reservoir of the replenishable stent.

25. A therapeutic agent delivery system as recited in claim 24 wherein said insertion means comprises a catheter-like tubular member.

26. A therapeutic agent delivery system as recited in claim 25 wherein said transfer means comprising a fitting corresponding to and mating with a fitting connected with the reservoir of the replenishable stent.

\* \* \* \* \*